United States Patent
Grunwald et al.

(10) Patent No.: US 11,122,990 B2
(45) Date of Patent: *Sep. 21, 2021

(54) APPARATUS AND METHOD FOR INTRAVASCULAR CATHETER NAVIGATION USING THE ELECTRICAL CONDUCTION SYSTEM OF THE HEART AND CONTROL ELECTRODES

(71) Applicant: Bard Access Systems, Inc., Salt Lake City, UT (US)

(72) Inventors: Sorin Grunwald, Paris (FR); Isabella B. Hurezan, Bucharest (RO)

(73) Assignee: Bard Access Systems, Inc., Salt Lake City, UT (US)

( * ) Notice: Subject to any disclaimer, the term of this patent is extended or adjusted under 35 U.S.C. 154(b) by 95 days.

This patent is subject to a terminal disclaimer.

(21) Appl. No.: 16/434,013

(22) Filed: Jun. 6, 2019

(65) Prior Publication Data

US 2019/0282122 A1 Sep. 19, 2019

Related U.S. Application Data

(63) Continuation of application No. 15/850,664, filed on Dec. 21, 2017, now Pat. No. 10,321,846, which is a continuation of application No. 14/678,986, filed on Apr. 5, 2015, now Pat. No. 9,854,992.

(60) Provisional application No. 61/977,120, filed on Apr. 9, 2014.

(51) Int. Cl.
*A61B 5/06* (2006.01)
*A61B 34/20* (2016.01)
*A61B 5/283* (2021.01)
*A61B 5/00* (2006.01)
*A61B 5/316* (2021.01)
*A61B 5/339* (2021.01)
*A61B 5/352* (2021.01)

(52) U.S. Cl.
CPC .............. *A61B 5/061* (2013.01); *A61B 5/283* (2021.01); *A61B 34/20* (2016.02); *A61B 5/316* (2021.01); *A61B 5/339* (2021.01); *A61B 5/352* (2021.01); *A61B 5/6822* (2013.01); *A61B 5/6823* (2013.01); *A61B 2034/2053* (2016.02)

(58) Field of Classification Search
CPC ........ A61B 5/061; A61B 5/6822; A61B 34/20
See application file for complete search history.

(56) References Cited

U.S. PATENT DOCUMENTS

| | | | |
|---|---|---|---|
| 8,388,546 B2 * | 3/2013 | Rothenberg | A61B 5/063 600/508 |
| 9,440,047 B1 * | 9/2016 | Elberse | A61B 5/352 |
| 9,445,746 B1 * | 9/2016 | Elberse | A61B 5/35 |
| 9,854,992 B2 * | 1/2018 | Grunwald | A61B 5/283 |
| 10,321,846 B2 * | 6/2019 | Grunwald | A61B 34/20 |

(Continued)

OTHER PUBLICATIONS

U.S. Appl. No. 14/678,986, filed Apr. 5, 2015, Non-Final Office Action dated May 15, 2017.

(Continued)

*Primary Examiner* — Eric D. Bertram
(74) *Attorney, Agent, or Firm* — Rutan & Tucker LLP

(57) ABSTRACT

A new apparatus, algorithm, and method are introduced herein to support navigation and placement of an intravascular catheter using the electrical conduction system of the heart (ECSH) and control electrodes placed on the patient's skin.

10 Claims, 6 Drawing Sheets

(56) References Cited

U.S. PATENT DOCUMENTS

2010/0317981 A1* 12/2010 Grunwald .............. A61B 5/349
                                                        600/509
2018/0110439 A1    4/2018 Grunwald et al.

OTHER PUBLICATIONS

U.S. Appl. No. 14/678,986, filed Apr. 5, 2015, Non-Final Office Action dated May 2, 2016.
U.S. Appl. No. 14/678,986, filed Apr. 5, 2015, Advisory Action dated Dec. 7, 2016.
U.S. Appl. No. 14/678,986, filed Apr. 5, 2015, Final Office Action dated Oct. 6, 2016.
U.S. Appl. No. 14/678,986, filed Apr. 5, 2015, Notice of Allowance dated Aug. 28, 2017.
U.S. Appl. No. 15/850,664, filed Dec. 21, 2017 Final Office Action dated Oct. 25, 2018.
U.S. Appl. No. 15/850,664, filed Dec. 21, 2017 Non-Final Office Action dated May 14, 2018.
U.S. Appl. No. 15/850,664, filed Dec. 21, 2017 Restriction Requirement dated Feb. 7, 2018.

* cited by examiner

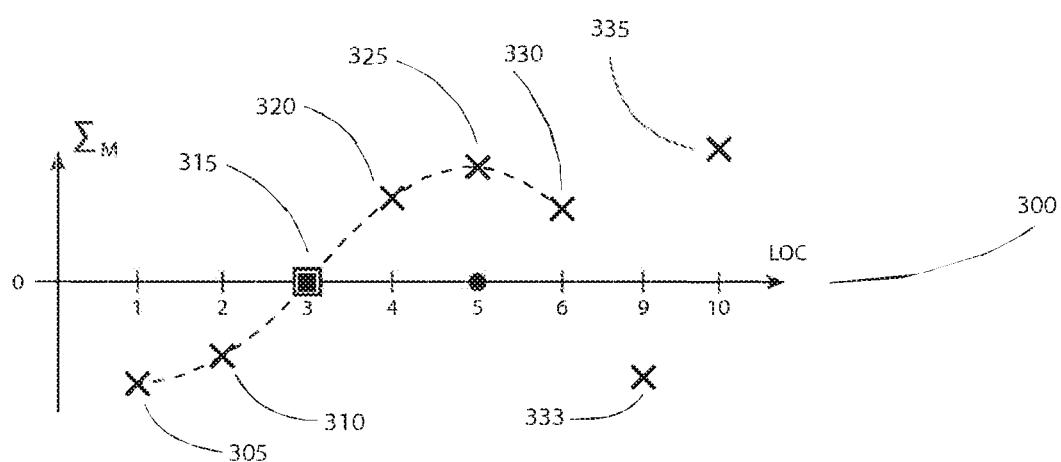
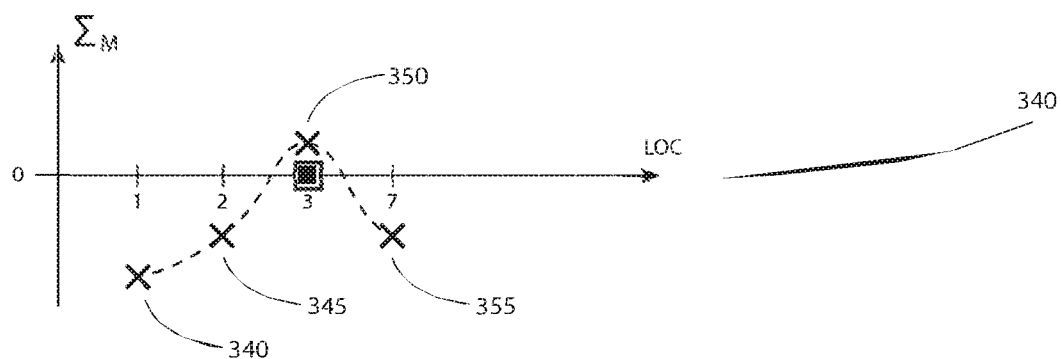
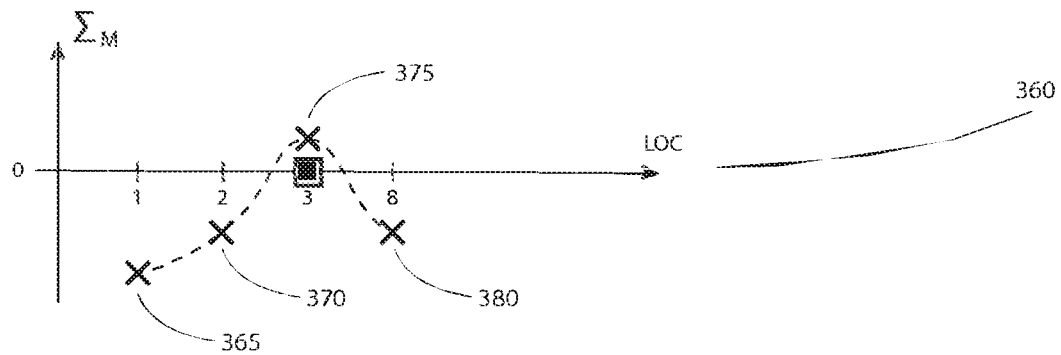
Fig. 3

Fig. 8

$$810 \quad S_x = \sqrt{\frac{\sum_{i=1}^{n}(x_i - \bar{x})^2}{n-1}}$$

$$820 \quad C_x = \sqrt{\frac{\sum_{j=1}^{n}(x_{i,j} - \bar{x}_i)(x_{i-1,j} - \bar{x}_{i-1})}{S_{x_i} S_{x_{i-1}}}}$$

$$830 \quad \Sigma_M = A_M + P_{M+} + P_{M-} + T_M$$

$$840 \quad \bar{x} = \frac{\sum_{i=1}^{n} x_i}{n}$$

APPARATUS AND METHOD FOR INTRAVASCULAR CATHETER NAVIGATION USING THE ELECTRICAL CONDUCTION SYSTEM OF THE HEART AND CONTROL ELECTRODES

PRIORITY

This application is a continuation of U.S. patent application Ser. No. 15/850,664, filed Dec. 21, 2017, now U.S. Pat. No. 10,321,846, which is a continuation of U.S. patent application Ser. No. 14/678,986, filed Apr. 5, 2015, now U.S. Pat. No. 9,854,992, which claims priority to U.S. Provisional Application No. 61/977,120, filed Apr. 9, 2014, each of which is incorporated by reference in its entirety into this application.

FIELD OF THE INVENTION

The Invention relates to the field of intravascular catheter navigation, tracking or guidance through the vasculature and of intravascular catheter tip location and placement. Currently, fluoroscopy can be used for both catheter navigation and tip location of intravascular catheters. In the case of central venous catheters, navigation support is currently provided by methods, such as fluoroscopy, magnetic, infrared, blood pressure or Doppler-based. ECG-based methods are used currently only for catheter tip location at the cavo-atrial junction in the proximity of the sinoatrial node. ECG-based methods are not currently used for catheter navigation or tip location at other locations in the vasculature or for catheter navigation. The purpose of the present Invention is to provide a single device for both intravascular catheter navigation and tip location at different locations in the vasculature, in the venous as well as in the arterial system without using X-ray or fluoroscopy.

BACKGROUND OF THE INVENTION

In many clinical situations it is essential to know the exact location of the tip of a catheter inserted in the body of a patient. It is also very helpful to be able to navigate the catheter through the patient's body, i.e., to follow the movements of the catheter tip, e.g., during catheter insertion. Currently, fluoroscopy can be used for catheter navigation and tip location of intravascular catheters. In the case of central venous catheters, navigation support is currently provided by methods, such as fluoroscopy, magnetic, or Doppler-based which have each their own benefits and limitations. ECG-based methods are used currently only for catheter tip location at the cavo-atrial junction in the proximity of the sinoatrial node. ECG-based methods are currently not used for catheter navigation.

There exists currently a need for an accurate, safe, intra-procedural and easy-to-use device, which allows, in a single device, for navigation and tip location of catheters at different locations in the vasculature, in the venous as well as in the arterial systems, which works for a wide range of catheter types and clinical applications, and which does not use radiation-based methods like X-ray and fluoroscopy.

A system and method for catheter mapping is described in U.S. Pat. No. 5,983,126, which uses a catheter equipped with at least a measuring electrode and a reference electrode on the patient to which triangulation signals are applied such that the a three-dimensional location of the catheter tip within the body can be calculated. U.S. Pat. No. 8,155,732 describes an ECG system for ECG signal measurement of intracardiac ECG using a switch and a processor to amplify the difference of a chest lead signal electronically connected to a catheter and a patient limb ECG signal in order to provide a catheter tip location signal without using any other surface ECG leads. U.S. Pat. No. 8,388,541 describes an integrated catheter placement system, which uses a magnetic tip location sensor for temporary placement on the patient's chest to detect the magnetic field of a stylet disposed in the a lumen of the catheter.

SUMMARY OF THE INVENTION

A new apparatus, algorithm, and method (all called Invention) are introduced herein to support navigation and placement of an intravascular catheter using the electrical conduction system of the heart (ECSH) and control electrodes placed on the patient's skin. According to the present Invention, an intravascular catheter can be guided both in the arterial and venous systems and positioned at different desired locations in the vasculature in a number of different clinical situations. The catheter is connected to the apparatus using, for example, sterile extension cables, such that the apparatus can measure the electrical activity at the tip of the catheter. Another electrode of the apparatus is placed for reference on the patient's skin. In one embodiment of the present Invention, a control electrode is placed on the patient's chest over the manubrium of the sternum below the presternal notch. In this case, if a catheter is inserted in the venous system, for example in the basilic vein, the Invention will indicate if the tip of the catheter navigates from the insertion point in the basilic vein into the subclavian vein on the same side, into the subclavian vein counter laterally, into the jugular vein, into the superior vena cava, into the cavoatrial junction (CAJ), into the right atrium (RA), into the right ventricle (RV), or into the inferior vena cava (IVC). For the same location of a control electrode, if a catheter is inserted in the arterial system, the Invention will indicate when the tip of the catheter is navigating into the arch of the aorta, into the right coronary artery, into the left circumflex artery, or into the left ventricle (LV).

In another embodiment of the present Invention, a control electrode can be placed on the sternum over the xiphoid process. In one embodiment of the present invention, a catheter can be inserted in the arterial systems by arterial radial, brachial or axillary access. In another embodiment of the present Invention, a catheter may be inserted into either the arterial or the venous systems by femoral or saphenous access.

In one aspect of the present Invention, navigation maps are introduced for different locations in the vasculature which allow for easy identification of the location of the catheter tip.

In another aspect of the present Invention, a novel algorithm is introduced to compute a navigation signal in real time using electrical signals from the tip of the catheter and from control electrodes.

In another aspect of the present Invention, a novel algorithm is introduced to compute in real time navigation parameters from the navigation signal computes according to the present Invention.

In another aspect of the present Invention, a method is introduced which makes use of the navigation signal to allow for placing an intravascular catheter at a desired location in the vasculature relative to the ECSH and to the control electrodes placed on the skin.

In another aspect of the present Invention, the electrical signals obtained from control electrodes and from the tip of the catheter may be generated by the natural ECSH, e.g., the sino-atrial node (SAN), by artificial (implanted) pacemakers or by electrical generators external to the body.

In yet another aspect of the Invention, an apparatus is introduced which supports data acquisition required by the computation of a navigation signal according to the present Invention.

BRIEF DESCRIPTION OF DRAWINGS

FIG. 3: Method of navigation to the CAJ based on navigation signals and navigation parameters calculated according to the present Invention for upper body venous access.

FIG. 8: Parameter computation algorithm according to the present Invention.

DETAILED DESCRIPTION

Figure 1:
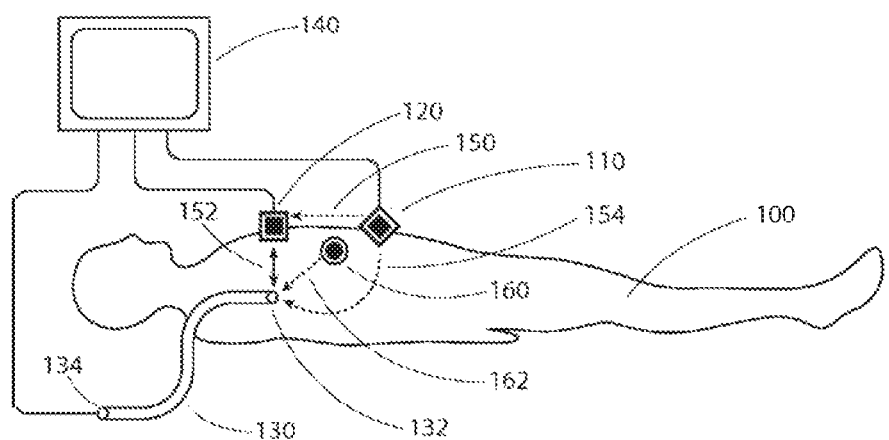
FIG. 1: Apparatus according to the present Invention connected to patient in supine position for access to the subclavian veins, internal jugular veins (IJ), SVC, CAJ, RA, IVC, and RV by upper body venous access or for access to the aortic arch, left heart and coronary arteries by arterial radial, brachial or axillary cannulation.

FIG. 1 illustrates the apparatus connected to a patient (100) in supine position for access to the subclavian veins, internal jugular veins (U), SVC, CAJ, RA, IVC, and RV by upper body venous access or for access to the aortic arch, left heart and coronary arteries by arterial radial, brachial or axillary cannulation. A control electrode (CE) (120) is positioned on the patient at a location of interest. This Invention allows for tracing the tip of an intravascular catheter relative to the CE and to the electrical conduction system of the heart (ECSH) (160).

The ECSH contains the following elements:
a) the sino-atrial node (SAN), whose electrical activity can be seen as the P wave or P segment on an ECG waveform,
b) the atrio-ventricular node (AVN) including the Bundle of His (BH), whose electrical activity can be seen as the PR segment on the ECG waveform
c) the Purkinje fibers (PF), whose electrical activity can be seen as the QRS complex on the ECG waveform
d) The ventricle myocardium (VM), whose repolarization includes the J wave, ST-segment, and the T- and U waves on the ECG waveform.

The natural/primary pacemaker of the heart is the SAN. It normal sinus rhythm, the SAN generates pulses at a rate of 100 times per minute. If the SAN does not function normally, the AVN and the BH will normally discharge and produces pulses at about 40-60 beats-per-minute. If the SAN and AVN both do not function normally, the PF will also produce spontaneous pulses at about 30-40 beats-per-minute. The AVN/BH and the PF can be considered secondary (ectopic) natural pacemakers. The reason the SAN normally controls the whole heart is that its pulses are released more often to the heart's muscle cells than those from AVN/BH or PF. With other words, under normal conditions, a pulse generated by the SAN passes down the ECSH and arrives before the other pacemakers have had a chance to generate their own spontaneous pulses. Nevertheless, under abnormal conditions in unhealthy hearts, e.g., arrhythmias, or, even in healthy hearts, in response to various stimulating events, e.g., overstimulation, the secondary pacemakers may also generate their own pulses. In such situations, secondary pacemakers can also be used for catheter navigation according to the present invention.

Another important aspect of the ECSH related to catheter navigation is the location of the different natural pacemakers in the heart walls relative to certain blood vessels. Thus, the SAN is located close to the junction between the SVC and the RA, i.e., at the upper end of the CAJ. Therefore, proximity to the SAN as measured using electrical signals at the tip of the catheter (P wave or P segment) may indicate a catheter tip location in the venous system at CM. The AVN is located between the atria and the ventricles, near the atrial septum and is supplied by blood coming through a branch of the right coronary artery and of the right of left circumflex arteries. Therefore, proximity to the AVN as measured using electrical signals at the tip of the catheter may indicate a catheter tip location in the arterial system in the right or circumflex coronary arteries. Further, certain modifications of the PR segment in the proximity of the AVN may indicate a position of the tip of the catheter in the aortic arch. Further, certain modifications of the QRS complex, of the ST segment and/or of the T and U waves may indicate a position of the tip of the catheter at specific locations in the ventricles, i.e., in the right ventricle in case of venous access or in the left ventricle in case of arterial access.

As the catheter navigates through the vasculature, the present Invention uses electrical signals generated by the ECSH to indicate where the catheter tip is relative to the ECSH and to the control electrodes. In one embodiment of this Invention illustrated in FIG. 1, the CE is placed on the manubrium of the sternum right below the presternal notch. This skin position is estimated to be the closest position on the skin corresponding to the upper end of the superior vena cava (SVC) in the vasculature. In addition, this position is easily identifiable by anatomical landmarks and is independent of the side of the vascular access location (left or right). For the same targeted position of the catheter tip in the vasculature, the CE may be placed at other locations on the skin, as well. The CE may be placed at other locations on the skin for different targeted positions of the catheter tip.

A reference electrode (RE) (110) is placed on the patient's skin. In one embodiment of the Invention, the RE is placed on the left lower patient abdomen right below the last rib. The RE may be placed at other locations, as well. A catheter (130) is inserted into the vasculature of the patient and electrical connectivity is ensured between the distal end of the catheter (132) and its proximal end (134). Such electrical conductivity can be ensured with currently available means, e.g., by using a conductive wire between the catheter ends or by injective electrically conductive solution like saline or heparin into the catheter. The proximal end of the catheter (134) is electrically connected to the apparatus (140) according to the present Invention. The CE (120) and the RE (110) are also electrically connected to the apparatus (140). The apparatus (140) measures an electrical signal (150) at the CE relative to the RE and another electrical signal (154) at the distal end of the catheter relative to the RE.

The apparatus, e.g., computer, computes navigation signals (152) and (162) based on the signal (154) obtained from the distal end of the catheter and from the signal (150) obtained from the CE. In one embodiment of the present Invention, the electrical signals obtained from the CE and from the tip of the catheter are generated by the ECSH (160), e.g., by the sino-atrial node. In another embodiment of the present invention, the electrical signals obtained from the CE and from the tip of the catheter are generated by artificial (implanted) pacemakers or by electrical generators external to the body.

Figure 2:
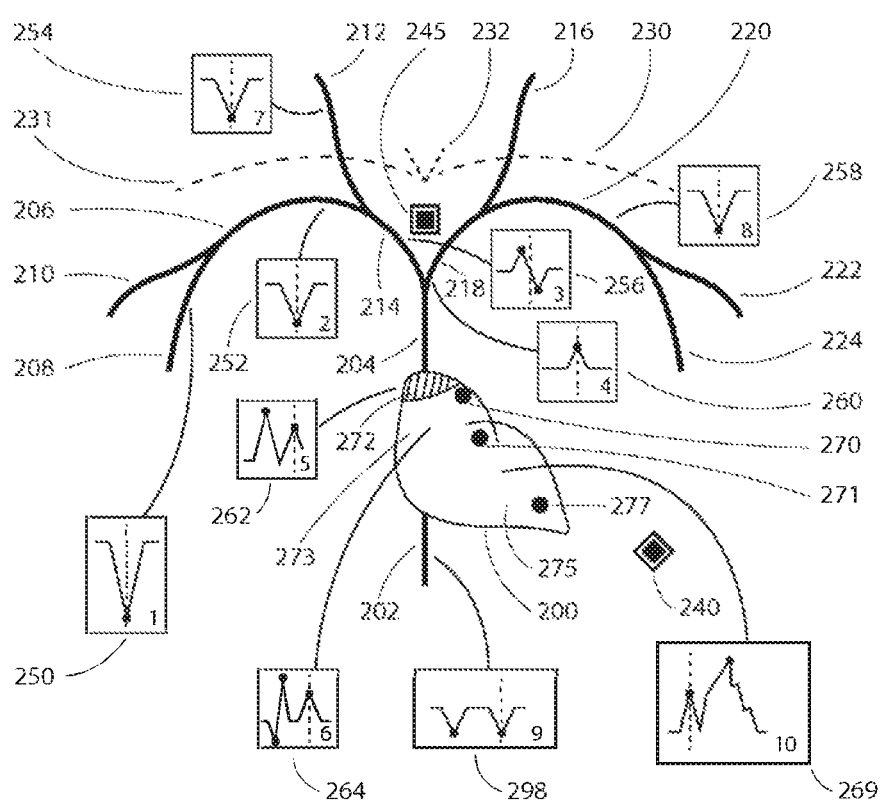
FIG. 2: Map of navigation signals for access to the subclavian veins, internal jugular veins (U), SVC, CAJ, RA, IVC, and RV for upper body venous access according to the present Invention.

FIG. 2 illustrates a map of navigation signals according to the present Invention for access to the subclavian veins, internal jugular veins (U), SVC, CAJ, RA, IVC, and RV for upper body venous access. The heart (200) and the venous system for the upper body are illustrated containing the following: inferior vena cava (202), superior vena cava (204), the left innominate (or brachiocephalic) vein (218), the right innominate (or brachiocephalic) vein (214), the left (220) and right (206) subclavian veins, the left (224) and right (208) brachial veins, the left (222) and right (210) axillary veins and the left (216), right (212) internal jugular veins, the CAJ (272), the RA (273), the RV (275), the SAN (270), the AVN/BH (271), and the PF (277). The anatomical landmarks illustrated in FIG. 2 are left (230) and right (231) clavicles and the presternal notch (232).

If a CE (245) is placed on the patient's skin right below the presternal notch over the manubrium of the sternum and an RE (240) is placed on the patient's skin right below the lowest left rib on the patient's abdomen then the illustrated navigations signals are computed and displayed according to the present Invention. In a brachial vein (208, 224), the navigation signal will present large negative amplitude aligned with the R-peak of the heart cycle (250). In a subclavian vein (206, 220), the navigation signal will present a smaller negative amplitude aligned with the R-peak (252, 258 respectively). Entering the innominate veins (214, 218) and approaching the CE (245) the navigation signal will result in a small biphasic navigation signal (256). At this location, the intravascular catheter tip is closest to the control electrode placed on the patient's skin. Ideally the signal at this catheter tip location should be zero indicating that the catheter tip is practically at the location with the control electrode. The real biphasic aspect of the navigation signal when the catheter tip is closest to the CE is a result of a difference in phase between the ECG waveform at the tip of the catheter and at the CE. The closer the tip of the catheter is to the CE, the smaller the phase difference illustrated by (256). This phase difference may be used according to the present Invention to determine when the catheter tip is closest to the CE and to analyze the trend of the catheter tip movements towards and away from the CE.

Advancing the catheter tip in the superior vena cava (204) will produce small positive amplitude aligned with the R-peak (260). In the jugular veins (212, 216), the navigation signal will have smaller negative amplitude aligned with the R-peak of the heart cycle (254), whereby the negative amplitude in the left jugular will be slightly larger than the negative amplitude in the right jugular due to the fact that the left jugular is further away from the SAN of the ECSH than the right jugular. The navigation signal computed at CAJ (272) is illustrated by (262) in FIG. 2. A large positive amplitude aligned with the P-segment of the heart cycle can be seen to the left of a small positive peak aligned with the R-peak of the heart cycle. Advancing the catheter into the RA (273) will result in the navigation signal illustrated in (264), FIG. 2 with a distinctive biphasic amplitude aligned with the P-segment of the heart cycle to the left of a small positive peak aligned with the R-peak. In the RV (275), the navigation signal is illustrated in FIG. 2 by (269), whereby a large amplitude aligned with the QRS complex and a large amplitude aligned with the T-wave indicate the proximity to the catheter tip of the AVN/BH or of the PF (277). The duration and sizes of the PR segment, QRS complex and of the T-wave will vary according to the specific location of the catheter tip in the RV, i.e., closer to the tricuspid valve (closer to the AVN/BH) or closer to the bottom of the RV (closer to the PF) or potentially in contact with the RV wall.

In one embodiment of the present invention, a weighted average or weighted difference (delta) of the CE and catheter tip signals is computed for the navigation signal. The weighted difference has the effect of diminishing the elements of the ECG waveform which are similar between the CE and the catheter tip and enhancing the elements of the ECG waveform which are different between the CE and the catheter tip. The similar elements are typically those static, i.e., not related to the catheter tip location. The different elements are typically those which change with the catheter tip location. For example, the R-peak of the ECG waveform is diminished, as is the T-wave if they do not depend on the catheter tip location. On the contrary, if they depend on the catheter tip location, the P-wave is enhanced and so are changes in the QRS complex or T-wave thus enhancing the ability to discriminate between changes in the navigation signal which are most relevant to catheter tip location changes.

These illustrations are not limitations of the present Invention. Other shapes of the navigation signals can be calculated as indicative of the locations in the vasculature. Such different shapes or variations of the navigation signal may depend on the location of the CE and the RE, may be a result of patient variability, of certain parameters of the computation algorithms, etc.

In another embodiment of the present Invention, a navigation map can be developed according to the present invention for catheter locations in the arterial system for the same placement of the CE and RE as in FIG. 2. The upper body access in the arterial access situation is performed by arterial radial, brachial or axillary cannulation. The catheter is then advanced into the aortic arch and then further into the coronary arteries. As the catheter tip approaches the aortic arch which is close to the CE, a biphasic navigation signal as the one illustrated in FIG. 2 (256) will be calculated according to the present Invention. As, for example, the catheter tip is advanced into the right coronary artery, which supplies the AVN/BH with blood, a specific change in the navigation signal in the PR segment and QRS complex will be noticeable. Further specific changes of the navigation signal according to the present Invention will be observed as the catheter tip is advanced into the coronaries, or into the descending aorta, or into the carotid arteries, or even into the pulmonary veins.

FIG. 3 illustrates a method of catheter tip navigation to the CAJ based on navigation signals calculated according to the present Invention for upper body venous access. In one embodiment of the present Invention, a CE and an RE are placed according to FIG. 2 and a catheter is inserted in a brachial vein (208,224). In one embodiment of the present invention, one navigation parameter is calculated as the sum $\Sigma_M$ of the relevant maximum amplitudes of the navigation signal for each heart cycle. $\Sigma_M$ is calculated according to equation (830) in FIG. 8, whereby $A_M$ is the maximum amplitude of the navigation signal aligned to the R-peak of the heart cycle, $P_{M+}$ is the maximum positive amplitude of the navigation signal aligned with the P-segment of the heart cycle, $P_{M-}$ is the maximum negative amplitude of the navigation signal aligned with the P-segment of the heart cycle, and $T_M$ is the maximum amplitude of the navigation signal aligned with the T-wave of the heart cycle. A biphasic navigation signal aligned with the P-wave of the heart cycle will contribute with both values $P_{M+}$ and $P_{M-}$ to $\Sigma_M$. In one embodiment of the present Invention, the algorithm calculates only one value $A_M$ aligned with the R-peak of the heart cycle and only one value $T_M$ aligned with the T-wave. $A_M$ and $T_M$ can be positive or negative.

Close to an access point in the brachial vein (208), the navigation signal computed according to the present invention (250) has a maximum negative amplitude of value $A_{M1}$. According to illustration (250), the navigation parameter $\Sigma_{M1}=A_{M1}$. This value is displayed on the graph (300) in FIG. 3 at location (abscissa) 1 (305). When the catheter is advanced into the subclavian vein (206), the maximum negative amplitude of the navigation signal decreases to $A_{M2}$ (252) and the navigation parameter $\Sigma_{M2}=A_{M2}$. This value is displayed on graph (300) at location (abscissa) 2 (310). The catheter is further advanced towards the innominate vein (214) right below the CE (245) and it reaches a location in the vasculature beneath the CE where the navigation signal is illustrated by (256). The maximum amplitude value ($A_{M3}$) aligned with the R-peak of the heart cycle is computed. It can have a small positive value, a small negative value or be practically zero. The value $\Sigma_{M3}=A_{M3}$ is displayed in graph (300) at location (abscissa) 3 (315).

In general, the maximum amplitude aligned with the R-peak when the catheter tip is closest to the CE, is minimal or close to zero. A small biphasic signal can also be an indication that the catheter tip is closest to the CE. If the catheter is further advanced in the superior vena cava (204), the navigation signal will show small a positive maximum amplitude aligned with the R-peak (260). The value of the navigation parameter in this case $\Sigma_{M4}=A_{M4}$ is displayed on graph 300 at location (abscissa) 4 (320). When the catheter tip reaches the CAJ, the navigation signal illustrated in FIG. 2 (262) has two maxima: one aligned with the R-peak ($A_{M5}$) and one aligned with the P-segment ($P_{M5+}$) of the heart cycle. Both maxima are in this case positive. The value of the navigation parameter at this catheter tip location $\Sigma_{M5}=A_{M5}+P_{M5+}$ is displayed on graph 300 at location (abscissa) 5 (325). When the catheter tip is advanced into the right atrium the signal at the tip of the catheter calculated according to the present Invention is illustrated in FIG. 2 (264). The navigation signal has a small positive maximum ($A_{M6}$) aligned with the R-peak of the heart cycle and a negative ($P_{M6-}$) and a positive maximum ($P_{M6+}$) values aligned with the P segment of the heart cycle. The value of the navigation parameter at this catheter tip location in the RA is $\Sigma_{M6}=A_{M6}+P_{M6+}+P_{M6-}$ and is displayed on graph 300 at location (abscissa) 6 (330). When the catheter tip is advanced into the IVC the signal at the tip of the catheter calculated according to the present Invention is illustrated in FIG. 2 (268). The navigation signal has a small negative maximum ($A_{M9}$) aligned with the R-peak of the heart cycle and a negative maximum ($P_{M9-}$) aligned with the P segment of the heart cycle. The value of the navigation parameter at this catheter tip location in the IVC is $\Sigma_{M9}=A_{M9}+P_{M9-}$ and is displayed on graph 300 at location (abscissa) 9 (333). When the catheter tip is advanced into the RV, the signal at the tip of the catheter calculated according to the present Invention is illustrated in FIG. 2 (269). The navigation signal has a positive maximum ($A_{M10}$) aligned with the R-peak of the heart cycle and a positive maximum ($T_{M10}$) aligned with the T segment of the heart cycle. In one embodiment of the present Invention, the value of the navigation parameter at this catheter tip location in the RV is calculated as $\Sigma_{M10}=A_{M10}+T_{M10}$ and is displayed on graph 300 at location (abscissa) 10 (335). In another embodiment of the present Invention, the value of the navigation parameter at this catheter tip location in the RV is calculated as $\Sigma_{M10a}=A_{M10a}$.

In a different situation, the catheter inserted in the brachial vein (208) can navigate into the subclavian vein (206), reach the innominate vein and then navigate into a jugular vein. When the catheter tip is in a jugular vein (212, 216), the navigation signal according to the present invention is illustrated by (254) and has a negative maximum value of $A_{M7}$. The sequence of catheter tip locations in this case is illustrated by graph (340) in FIG. 3. The value $\Sigma_{M1}=A_{M1}$ of the navigation parameter obtained when the catheter is inserted in the brachial vein is represented as (340), the value $\Sigma_{M2}=A_{M2}$ in the subclavian vein as (345), the value $\Sigma_{M3}=A_{M1}$ at the point closest to the CE as (350), and, finally, the value $\Sigma_{M7}=A_{M7}$ in the jugular vein at location (abscissa) 7 as (355).

In yet a different situation, the catheter inserted in the brachial vein (208) can navigate into the subclavian vein (206), reach the innominate vein and then navigate into the contralateral subclavian vein (220). When the catheter tip is in the contralateral subclavian vein, the navigation signal according to the present invention is illustrated by (258) and has a negative maximum value of $A_{M8}$. The sequence of catheter tip locations in this case is illustrated by graph (360) in FIG. 3. The value $\Sigma_{M1}=A_{M1}$ when the catheter is inserted in the brachial vein is represented as (365), the value in the subclavian vein $\Sigma_{M2}=A_{M2}$ as (370), the value $\Sigma_{M3}=A_{M3}$ at the point closest to the CE as (375), and, finally, the value $\Sigma_{M8}=A_{M8}$ in the contralateral subclavian vein at location 8 as (380).

From these illustrations and embodiments it can be seen that the navigation signal and the navigation parameter calculated according to the present Invention can be used to navigate the catheter towards and place the catheter tip at certain locations in the vasculature, in particular in and around the heart. In order to achieve this goal, the present Invention introduces a new catheter navigation and positioning method, which in one embodiment consists of the following steps:

1. Place a reference electrode on the patient's left lower abdomen, e.g. right below the lowest rib. Make an electrical connection between the electrode and the apparatus according to the present invention.
2. Place a control electrode on the patient's skin in a position relevant to the target location for the catheter tip in the vasculature, e.g., below the sternal notch over the manubrium of the sternum. Make an electrical connection between the control electrode and the apparatus according to the present invention.
3. Insert the catheter in the vasculature (artery or vein) according to standard clinical procedures.
4. Make an electrical connection between the distal end of the catheter (catheter tip), the proximal end of the catheter and the apparatus according to standard clinical procedures.

5. Watch the navigation signal provided by the apparatus according to the present Invention.
6. Watch the amplitude of the signal aligned with the R-peak of the heart cycle and follow the map of the navigation signal according to the present invention in order to estimate the location of the catheter tip relative to the control electrode.
7. Watch the amplitude or amplitudes of the signal aligned with the P segment of the heart cycle and follow the map of the navigation signal according to the present invention in order to estimate the location of the catheter tip relative to the CAJ.
8. Watch the amplitude of the signal aligned with the QRS complex and the T segment of the heart cycle and follow the map of the navigation signal according to the present invention in order to estimate the location of the catheter tip relative to the ventricles.
9. Watch the amplitude of the signal aligned with the QRS complex and with the PR segment and follow the map of the navigation signal according to the present invention in order to estimate the location of the catheter tip relative to the coronary arteries and the aortic arch.
10. Choose your desired catheter tip location based on the navigation map according to the present Invention and place the catheter tip at that location.
11. Finish the catheter placement procedures according to the standard clinical procedures.

The herein presented embodiment of the catheter navigation and positioning method is not a limitation of the current Invention. Other embodiments and variations of this method are possible which are obvious to those skilled in the art.

Figure 4:
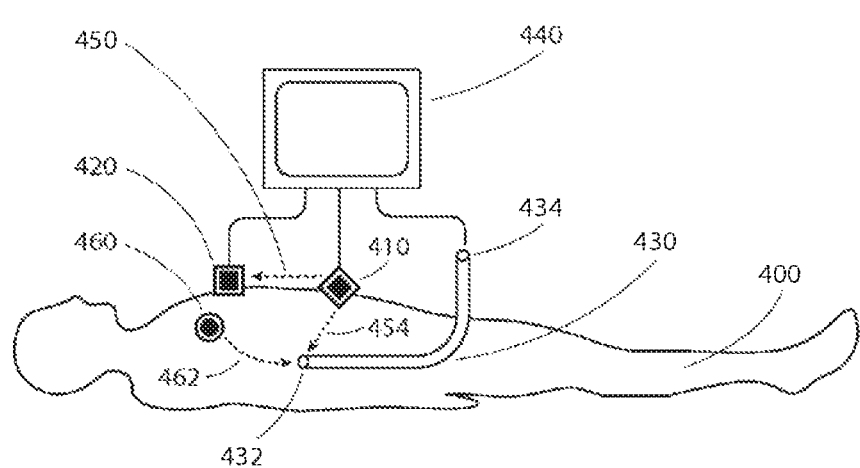
FIG. 4: Apparatus according to the present Invention connected to patient in supine position for cannulation of the femoral or saphenous veins or of the femoral artery

FIG. 4 illustrates the apparatus connected to patient in supine position for cannulation of the femoral vein or femoral artery. A CE (420) is positioned on the patient at a location of interest. In one embodiment of this Invention illustrated in FIG. 2, the CE is placed on the patient's sternum over the xiphoid process. This skin position is estimated to be the closest position on the skin corresponding in the vasculature to the inferior vena cava (IVC) below the heart. In addition, this position is easily identifiable by anatomical landmarks and is independent of the side of the femoral vascular access location (left or right). For the same targeted position of the catheter tip in the vasculature, the CE may be placed at other locations on the skin, as well. The CE may be placed at other locations on the skin for different targeted positions of the catheter tip.

An RE (410) is placed on the patient's skin. In one embodiment of the Invention, the RE is placed on the left lower patient abdomen right below the lowest rib. The RE may be placed at other locations, as well. A catheter (430) is inserted into the vasculature of the patient by femoral access and electrical connectivity is ensured between the distal end of the catheter (432) and its proximal end (434). Such electrical conductivity can be ensured with currently available means, e.g., by using a conductive wire between the catheter ends or by injective electrically conductive solution like saline or heparin into the catheter. The proximal end of the catheter (434) is electrically connected to the apparatus (440) according to the present Invention. The CE (420) and the RE (410) are also electrically connected to the apparatus (440). The apparatus (440) measures an electrical signal (450) at the CE relative to the RE and another electrical signal (454) at the distal end of the catheter relative to the RE.

The apparatus computes a navigation signal based on the signal (454) obtained from the distal end of the catheter and from the signal (450) obtained from the CE. The signal (454) at the catheter tip is, in certain locations in the vasculature, determined by the ECSH, for example by a natural pacemaker of the heart (460) and the relative location of the catheter tip (462) to this pacemaker. The electrical signals obtained from the CE and from the tip of the catheter may be generated by the natural body pacemakers, e.g., the sino-atrial node or the atrio-ventricular node, by artificial (implanted) pacemakers or by electrical generators external to the body.

Figure 5:
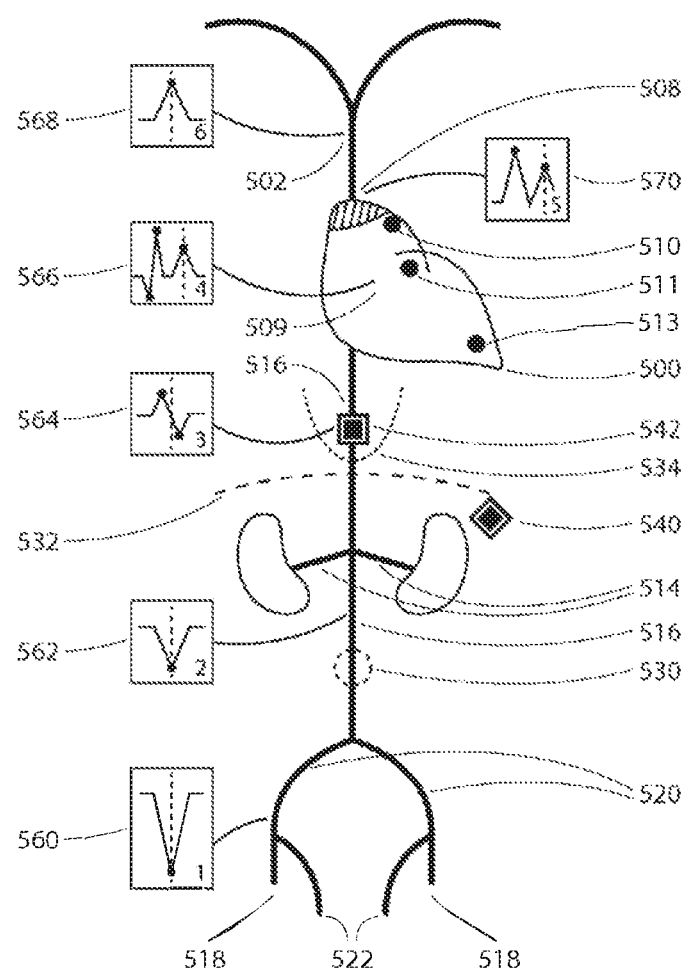
FIG. 5: Map of navigation signals for access to the superior subclavian veins, internal jugular veins (U), SVC, CAJ, RA, IVC, and RV for femoral or saphenous venous access according to the present Invention

FIG. 5 illustrates a map of navigation signals according to the present Invention for navigation to the CAJ, RA, IVC, and RV in the case of femoral or saphenous venous access. Besides the heart (500), the superior vena cava (502), and the left (504) and right (506) subclavian veins, FIG. 5 illustrates the following elements of the venous system and of the ECSH: the CAJ (508), the RA (509), the SAN (510), the AVN/BH (511), the PF (513), in addition to the inferior vena cava (516), the hepatic veins (512), the renal veins (514), the femoral veins (518), the iliac veins (520), and the saphenous veins (522). The illustrated anatomical landmarks are: the xiphoid process (534), the right and left lowest ribs (532), and the umbilicus (530).

If an CE (542) is placed on the patient's sternum over the xiphoid process (534) and an RE (540) is placed right below the lowest left rib on the patient's left abdomen then the illustrated navigations signals are computed and displayed according to the present Invention. In a femoral or saphenous vein (518 or 522), the navigation signal will present large negative amplitude aligned with the R-peak of the heart cycle (560). In an iliac vein or in the inferior vena cava just about the junction with the iliac veins, the navigation signal will present smaller negative amplitude aligned with the R-peak (562). Advancing the catheter tip into the inferior vena cava (516) and approaching the CE (542) will result in a small biphasic navigation signal (564). The biphasic aspect of the navigation signal when the catheter tip is closest to the CE is a result of a difference in phase between the ECG waveforms at the tip of the catheter and at the CE. The closer the tip of the catheter is to the CE, the smaller the phase difference illustrated by (564). This phase difference may be used according to the present Invention to determine when the catheter tip is closest to the CE and to analyze the trend of the catheter tip movements towards and away from the CE. Further advancing the catheter tip into the right atrium (509) will result in a navigation signal (566) with a small positive peak aligned with the R-peak of the heart cycle and with a biphasic signal aligned with the P segment of the hear cycle having one negative and one positive maximum values (566). When the catheter tip reaches the CAJ (508), the navigation signal is illustrated by (570) with a maximum positive value aligned with the R-peak and one maximum positive value aligned with the P segment of the heart cycle. If the catheter is advanced into the SVC, the navigation signal (568) will show a small positive maximum value aligned with the R-peak of the heart cycle.

These illustrations are not limitations of the present Invention. Other shapes of the navigation signals can be calculated as indicative of the locations in the vasculature. Such different shapes or variations of the navigation signal may depend on the location of the CE and the RE, may be a result of patient variability, of certain parameters of the computation algorithms, etc.

In another embodiment of the present Invention, a navigation map can be developed according to the present invention for catheter locations in the arterial system for the same placement of the CE and RE as in FIG. 5. The arterial access in the arterial access situation is performed by femoral cannulation. The catheter is then advanced into the abdominal aorta, into the descending aorta, into the aortic arch and then further into the coronary arteries. As the catheter tip approaches the end of the abdominal aorta and the beginning of the descending aorta which is closest to the CE, a biphasic navigation signal as the one illustrated in FIG. 5 (564) will be calculated according to the present Invention. As, for example, the catheter tip is advanced into the right coronary artery, which supplies the AVN/BH with blood, a specific change in the navigation signal in the PR segment and QRS complex will be noticeable. Further specific changes of the navigation signal according to the present Invention will be observed as the catheter tip is advanced into the coronaries, or into the descending aorta, or into the carotid arteries, or even into the pulmonary veins.

Figure 6:
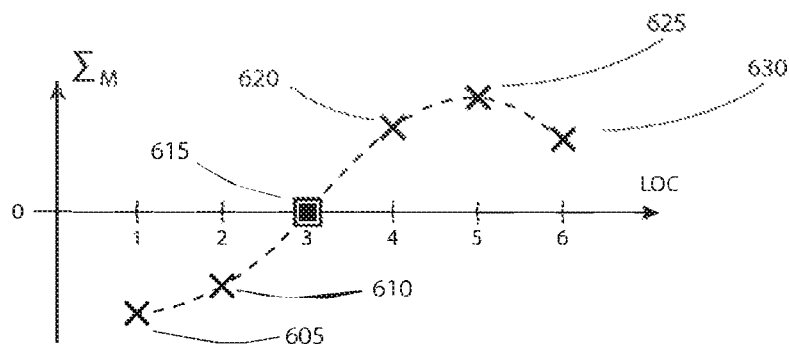
FIG. 6: Method of navigation to the CAJ based on navigation signals and navigation parameters calculated according to the present Invention for femoral or saphenous venous access.

FIG. 6 illustrates a method of navigation to the CAJ based on navigation signals calculated according to the present Invention for saphenous or femoral venous access. In one embodiment of the present invention a navigation parameter is calculated as the sum $\Sigma_M$ of relevant maximum amplitudes of the navigation signal for each heart cycle. $\Sigma_M$ is calculated according to equation (830) in FIG. 8, whereby $A_M$ is the maximum amplitude of the navigation signal aligned to the R-peak of the heart cycle, $P_{M+}$ is the maximum positive amplitude of the navigation signal aligned with the P-segment of the heart cycle, $P_{M-}$ is the maximum negative amplitude of the navigation signal aligned with the P-segment of the heart cycle, and $T_M$ is the maximum amplitude of the navigation signal aligned with the T-wave of the heart cycle. A biphasic navigation signal aligned with the P-wave will contribute with both values $P_{M+}$ and $P_{M-}$ to $\Sigma_M$. In one embodiment of the present invention, the algorithm calculates only one value $A_M$ aligned with the R-peak of the heart cycle and only one $T_M$ value aligned with the T-wave of the heart cycle. $A_M$ and $T_M$ can be positive or negative.

Close to the femoral or saphenous access point, the navigation signal computed according to the present invention (560) has a maximum negative amplitude of value $A_{M1}$. According to illustration (560), the navigation parameter at this catheter tip location is $\Sigma_{M1}=A_{M1}$. This value is displayed on the graph (600) in FIG. 6 at location (abscissa) 1 (605). When the catheter is advanced into the IVC (516), the maximum negative amplitude of the navigation signal decreases to $A_{M2}$ (562) and $\Sigma_{M2}=A_{M2}$. This value is displayed on graph (600) at location (abscissa) 2 (610). The catheter is further advanced towards the CE and it reaches a location in the vasculature beneath the CE where the navigation signal is illustrated by (564). The maximum amplitude value ($A_{M3}$) aligned with the R-peak of the heart cycle is computed according to the present invention. The navigation signal can have a small positive value, a small negative value or be practically zero. The value $\Sigma_{M3}=A_{M3}$ is displayed in graph (600) at location (abscissa) 3 (615). In general, the maximum navigation signal amplitude aligned with the R-peak when the catheter tip is closest to the CE, is minimal or close to zero. A small biphasic signal can also be an indication that the catheter tip is closest to the CE. If the catheter is further advanced in the RA (509), the signal at the tip of the catheter calculated according to the present Invention is illustrated in FIG. 5 (566).

The navigation signal has a small positive maximum ($A_{M4}$) aligned with the R-peak of the heart cycle and a negative ($P_{M4-}$) and a positive maximum ($P_{M4+}$) values aligned with the P segment of the heart cycle. The value of the navigation parameter at this catheter tip location in the RA is $\Sigma_{M4}=A_{M4}+P_{M4+}+P_{M4-}$ and is displayed on graph 600 at location (abscissa) 4 (620). When the catheter tip reaches the CAJ (508), the navigation signal illustrated in FIG. 5 (570) has two maxima: one aligned with the R-peak ($A_{M5}$) and one aligned with the P-segment ($P_{M5+}$) of the heart cycle. Both maxima are in this case positive. The value of the navigation parameter at this catheter tip location $\Sigma_{M5}=A_{M5}+P_{M5+}$ is displayed on graph 600 at location (abscissa) 5 (625). When the catheter tip is advanced into the SVC the signal at the tip of the catheter calculated according to the present Invention is illustrated in FIG. 5 (568). The navigation signal has a small positive maximum ($A_{M6}$) aligned with the R-peak of the heart cycle. The value of the navigation signal at this catheter tip location in the SVC is $\Sigma_{M6}=A_{M6}$ and is displayed on graph 600 at location (abscissa) 6 (630).

From these illustrations and embodiments it can be seen that the navigation signal calculated according to the present Invention can be used to navigate the catheter towards and place the catheter tip at certain locations in the vasculature, in particular in and around the heart. In order to achieve this goal, the present Invention introduces a catheter navigation and positioning method, which in one embodiment consists of the following steps:

1. Place a reference electrode on the patient's left lower abdomen, e.g. right below the lowest rib. Make an electrical connection between the electrode and the apparatus according to the present invention.
2. Place a control electrode on the patient's skin in a position relevant to the target location for the catheter tip in the vasculature, e.g., on the patient's sternum over the xiphoid process. Make an electrical connection between the control electrode and the apparatus according to the present invention.
3. Insert the catheter in the vasculature (artery or vein) by femoral or saphenous access according to standard clinical procedures.
4. Make an electrical connection between the distal end of the catheter (catheter tip), the proximal end of the catheter and the apparatus according to standard clinical procedures.
5. Watch the navigation signal provided by the apparatus according to the present Invention.
6. Watch the amplitude of the signal aligned with the R-peak of the heart cycle and follow the map of the navigation signal according to the present invention in order to estimate the location of the catheter tip relative to the control electrode.
7. Watch the amplitude or amplitudes of the signal aligned with the P segment of the heart cycle and follow the map of the navigation signal according to the present invention in order to estimate the location of the catheter tip relative to the CAJ.
8. Watch the amplitude of the signal aligned with the QRS complex and the T segment of the heart cycle and follow the map of the navigation signal according to the present invention in order to estimate the location of the catheter tip relative to the ventricles.
9. Watch the amplitude of the signal aligned with the QRS complex and with the PR segment and follow the map of the navigation signal according to the present invention in order to estimate the location of the catheter tip relative to the coronary arteries and the aortic arch.
10. Choose your desired catheter tip location based on the navigation map according to the present Invention and place the catheter tip at that location.
11. Finish the catheter placement procedures according to the standard clinical procedures.

The herein presented embodiment of the catheter navigation and positioning method is not a limitation of the current Invention. Other embodiments and variations of this method are possible which are obvious to those skilled in the art.

Figure 7:
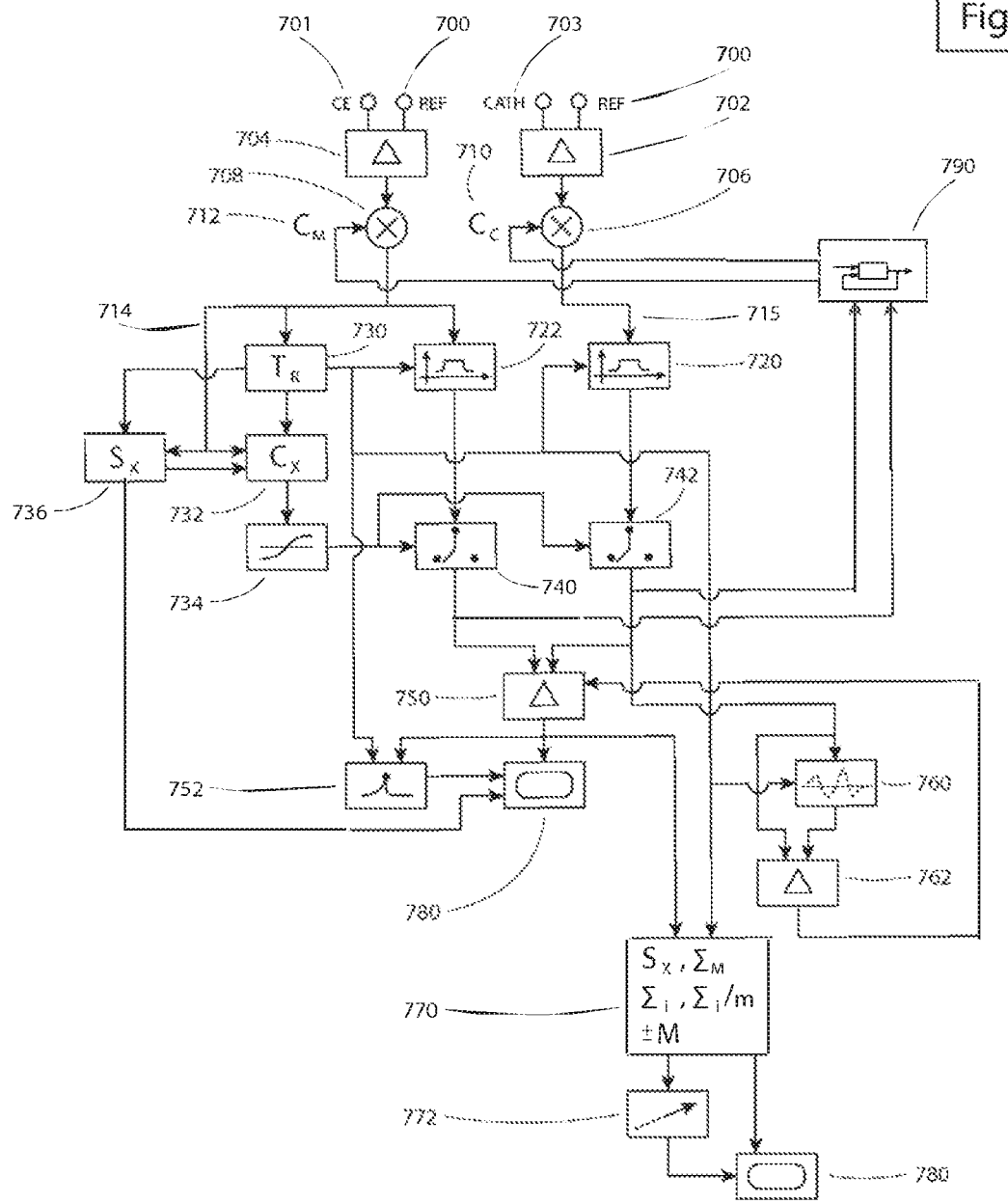
FIG. 7: Flow chart and algorithm generating navigation signals and navigation parameters according to the present Invention.

FIG. 7 illustrates the flow chart for generating navigation signals and parameters according to the present Invention. Electrical signals from a CE (701) and from an RE (700) are input to a measurement unit (704). The electrical signals from an RE (700) and from the tip of the catheter CATH (703) are input to another measurement unit (702). Any number of such measurement units can be implemented for any number of CEs and any number of catheter sensors. The reference electrode can be the same for any number of such measurement units or there can be different reference electrodes for different measurement units. The signal generated by (704) is weighted with a coefficient CM (712) by the multiplication unit (708) and the signal generated by (702) is weighted with another coefficient CC (710) by the multiplication unit (706). CM and CC may be equal or different in value. The CM and CC values can be fixed or adaptive as a result of the analysis of the signals performed by the signal analysis unit (790), which acts as an active feedback loop.

In one embodiment of the present Invention, the signal (714), which originates at a CE is used by the peak detector unit TR (730) to detect the timing of the R-peak of the QRS complex of each heart cycle. In one embodiment of the present Invention, the TR unit (730) also calculates the duration of a heart cycle, i.e., the time interval between two R-peaks. In one embodiment of the present Invention, the TR unit further calculates the heart rate. In one embodiment of the present Invention, the TR unit further calculates the number of data samples in a heart cycle using the duration of the heart cycle and the sampling rate for sampling/digitizing the navigation signal. The timing of the R-peak is used to synchronize and trigger different computations according to the present Invention. The timing of the R-peak can be also displayed together with the navigation signal and with navigation parameters calculated according to the present Invention on the monitor (780).

In one embodiment of the present Invention, the unit (736) computes the standard deviation S, of the navigation signal for each heart cycle according to equations (810) and (840) in FIG. 8. In one embodiment of the present Invention, the value of the standard deviation can be used as a navigation parameter and can displayed on the monitor (780). In one embodiment of the present Invention, the unit (732) computes the auto-correlation Cx of the navigation signal for each heart cycle according to (820), (810), and (840) in FIG. 8. In one embodiment of the present Invention, the value Cx of the auto-correlation is analyzed by a threshold detector (734) and used to filter out certain heart cycles using the switches (740) and (742). A high value of the auto-correlation Cx may indicate a stable signal, while a low value of the auto-correlation Cx may indicate large variations between heart cycles due, for example, to noise. In one embodiment of the present Invention, if the auto-correlation value Cx is lower than a certain threshold, the heart cycle with that low auto-correlation value Cx is excluded from further computations because it may not be relevant due to high variability of the signal.

In one embodiment of the present Invention, the timing calculated by the TR unit (730) is used to trigger low-pass, band-pass, high-pass or selective filtering related to one or more heart cycles or to fractions of the heart cycle by the filter units (722) and (720). Such filtering may be different for the signals originating at a CE and at the catheter tip.

The unit (750) computes the difference signal between the signals originating at a CE and at the catheter tip. In one embodiment of the present invention, a weighted average or weighted difference of the CE and catheter tip signal or signals is computed by the unit (750) in order to generate a navigation signal. The weighted difference has the effect of diminishing the elements of the ECG waveform which are similar between the CE and the catheter tip and thus enhancing the elements of the ECG waveform which are different. The similar elements are typically those static, i.e., not related to the catheter tip location. The different elements are typically those which change with the catheter tip location. For example, the R-peak of the ECG waveform is diminished, as is the T-wave if they do not change as a function of the catheter tip location. On the contrary, the P-wave changes are enhanced and so are changes in the QRS complex or T-wave if these changes are related to the catheter tip location. Thus the unit (750) enhances the ability to discriminate between changes in the navigation signal which are relevant to catheter tip location changes.

In one embodiment of the present Invention, the difference signal is displayed on the monitor (780). In one embodiment of the present Invention, the unit (752) computes the peak of the navigation signal $A_M$, and uses the timing of the R-peak of the heart cycle to display information about the synchronization between the navigation signal and the heart cycle onto on the monitor (780).

In one embodiment of the present Invention, the unit (760) in FIG. 7 detects baseline changes in the signal originating at the catheter tip and the unit (762) subtracts the baseline changes from the signal. The baseline removal function performed by units (760) and (762) is different from standard filtering for baseline removal as known in the art. The baseline removal function performed by units (760) and (762) detects and removes such baseline variations which may occur due to catheter navigation, i.e., due to the fact that the electrical signal at the tip of the catheter is measured at different locations which may be characterized by different levels of the baseline.

In one embodiment of the present Invention, the parameter computation unit (770) computes several quantitative navigation parameters from the navigation signal:

a) The standard deviation of the ECG waveform during a heart cycle and/or during a sequence of heart cycles and/or for a certain time segment within a heart cycle, e.g., the P-segment computed according to (810) in FIG. 8.
  b) The sum of maximum relevant amplitudes of the navigation signal for each heart cycle ΣM computed according to (830) in FIG. 8.
  c) The average value of the navigation signal for a heart cycle and/or for a sequence of heart cycles and/or for a certain time segment within a heart cycle, e.g., the P-segment computed according to (840) in FIG. 8.
  d) The relevant maximum amplitudes in a heart cycle: $A_M$ (the maximum amplitude of the navigation signal aligned with R-peak of the heart cycle), $P_{M-}$ (the maximum negative amplitude of the navigation signal aligned with the P-segment of the heart cycle), $P_{M+}$ (the maximum positive amplitude of the navigation signal aligned with the P-segment of the heart cycle), and TM (the maximum amplitude of the navigation signal aligned with the T-wave of the heart cycle).
  e) The sum $\Sigma_i$ of the sample values of the navigation signal for a heart cycle and/or for a sequence of heart cycles and/or for a certain time segment within a heart cycle, e.g., the P-segment. The sum $\Sigma_t$ is equivalent to the area (integral) under the navigation signal in the navigation signal graph.

The herein illustrated quantitative parameters are not a limitation of the current Invention. Other parameters and variations of these parameters are possible which are obvious to those skilled in the art.

In one embodiment of the present invention, these navigation parameters are displayed on the monitor (780). In one embodiment of the present Invention, the navigation parameters computed by (770) are input to a direction evaluation unit (772) which analyzes these parameters in order to detect a certain trend or direction in the catheter tip movements. For example, in one embodiment of the present Invention, the direction evaluation unit (772) determines if the catheter tip is moving towards or away from a CE by analyzing the succession of relevant maximum amplitudes aligned with the R-peak of the heart cycle and by determining when the navigation signal is biphasic and minimal in a certain succession. In another embodiment of the present Invention, the direction evaluation unit (772) determines if the catheter tip is moving towards or away from the CAJ by analyzing the succession of the values of the navigation parameter M.

In one embodiment of the present Invention, one parameter used for navigation is the auto-correlation calculated according to (820) in FIG. 8. In one embodiment of the present Invention, one parameter used for navigation is the sum of maximum relevant amplitudes of the navigation signal for each heart cycle M. The sum $\Sigma_M$ is calculated according to equation (830) in FIG. 8, whereby $A_M$ is the maximum amplitude of the navigation signal aligned to the R-peak of the heart cycle, $P_{M+}$ is the maximum positive amplitude of the navigation signal aligned with the P-segment of the heart cycle, $P_{M-}$ is the maximum negative amplitude of the navigation signal aligned with the P-segment of the heart cycle, and $T_M$ is the maximum amplitude of the navigation signal aligned to the T-wave of the heart cycle. A biphasic P-wave will contribute with both values $P_{M+}$ and $P_{M-}$ to $\Sigma_M$. There exists only one value $A_M$ aligned with the R-peak of the heart cycle. $A_M$ and TM can be positive or negative. In one embodiment of the present Invention, one parameter used for navigation is the sum of all signal samples $\Sigma_t$ for a given time period of time. In one embodiment of the present invention, the average value of the navigation signal over a certain period of time is computed according to (840) in FIG. 8.

In one embodiment of the present Invention, relevant positive and negative amplitudes and their timing relative to the R-peak of the heart cycle are computed for each heart cycle from the navigation signal, e.g., $A_M$ is the maximum amplitude of the navigation signal aligned to the R-peak of the heart cycle, $P_{M+}$ is the maximum positive amplitude of the navigation signal aligned with the P-segment of the heart cycle, $P_{M-}$ is the maximum negative amplitude of the navigation signal aligned with the P-segment of the heart cycle, and $T_M$ is the maximum amplitude of the navigation signal aligned to the T-wave of the heart cycle. Each and all of these parameters can be computed according to the present Invention, for one heart cycle, and/or for several heart cycles, and/or or for a fraction of a heart cycle, e.g., for the P segment (the time period corresponding to the P-wave).

The illustration in FIG. 7 is not a limitation of the current invention. Someone skilled in the art will find it obvious that other solutions are possible to obtain the same results. Moreover, for someone skilled in the art it will be obvious that elements and units illustrated in FIG. 7 can be practically implemented in hardware and/or firmware and/or software with alternative but equivalent solutions.

FIG. 8 illustrates parameter computation methods according to the present Invention. In one embodiment of the present Invention, the standard deviation of the navigation signal $Sx_j$ is computed according to (810), whereby n represents the number n of data samples xi for the j-th heart cycle, i=1,n. The value −x represents the average value of the data samples over the j-th heart cycle (840). The standard deviation computed according to (810) is a measure of the variations of the navigation signal values around its average value during a heart cycle. For example, when the catheter tip is further away from the $C_E$, then the value of the standard deviation $Sx_j$ is larger than the value of the standard deviation $Sx_k$ when the catheter tip is closest to the $C_E$. Thus, the value of the standard deviation calculated according to the present Invention can be used as a measure of the proximity of the catheter tip to the $C_E$.

In one embodiment of the present Invention, the auto-correlation coefficient $Cx_{j,j-1}$ is computed according to (820) for the navigation signal x at the j-th heart cycle and at the previous j−1-the heart cycle, whereby n represents the number of data samples xi for the j-th heart cycle, i=1,n. The value $^-x_j$ represents the average value of the data samples over the j-th heart cycle computed according to (840). The value $^-x_{j-1}$ represents the average value of the data samples over the j−1-th heart cycle, i.e., of the one heart cycle before the j-th heart cycle. $Sx_j$ is the standard deviation of the navigation signal computed according to (810) for the j-th heart cycle. $Sx_{j-1}$ is the standard deviation of the navigation signal computed according to (810) for the j-th heart cycle. In general, the number of samples n for the j-th heart cycle is different than the number of samples for the j-th heart cycle. According to the present Invention, n samples are considered for the calculation of both $Sx_j$ and $Sx_{j-1}$, whereby n is the number of samples of the j-th heart cycle. The n samples for the calculation of $Sx_{j-1}$ are selected starting from the end of the j−1-th heart cycle as determined by the TR unit (730) in FIG. 7. In another embodiment of the Invention, the auto-correlation coefficient can be calculated using (820) as $Cx_{j,k}$, whereby j and k are any two heart cycles. This includes the situation in which j=k and the coefficient is calculated for the same heart cycle.

In one embodiment of the present Invention, one parameter used for navigation is the sum of maximum amplitudes of the navigation signal for each heart cycle M. In one embodiment of the present Invention, the sum $\Sigma_M$ is calculated according to equation (830) in FIG. 8, whereby $A_M$ is the maximum amplitude of the navigation signal aligned to the R-peak of the heart cycle, $P_{M+}$ is the maximum positive amplitude of the navigation signal aligned with the P-segment of the heart cycle, $P_{M-}$ is the maximum negative amplitude of the navigation signal aligned with the P-segment of the heart cycle, and $T_M$ is the maximum amplitude of the navigation signal aligned to the T-wave of the heart cycle. A biphasic navigation signal aligned with the P-segment of the heart cycle will contribute with both values $P_{M+}$ and $P_{M-}$ to $\Sigma_M$. In one embodiment of the present Invention, the algorithm computes only one value $A_M$ aligned with the R-peak of the heart cycle and only one $T_M$ value aligned with the T-wave of the heart cycle. $A_M$ and $T_M$ can be positive or negative. In another embodiment of the present Invention, the sum $\Sigma_M$ is calculated as:

$$\Sigma_M = A_M + P_{M+} + P_{M-}.$$

In one embodiment of the present Invention, the navigation parameters in FIG. 8, i.e., the standard deviation (810), the auto-correlation (820), the sum of relevant amplitudes (830), and the average value (840) are computed for a heart cycle. In another embodiment of the present Invention, the navigation parameters in FIG. 8 are computed for several consecutive heart cycles. In another embodiment of the present Invention, the navigation parameters in FIG. 8 are computed for a fraction of a heart cycle, e.g., only for an interval/segment of interest within a heart cycle, e.g., for the P segment.

What is claimed is:

1. An intravascular catheter navigation device, comprising:
   a computer comprising a monitor and a plurality of measurement and computing units;
   a control electrode electrically connected to the computer, the control electrode designed for placement on a sternum of a patient over a xiphoid process;
   a catheter including a tip electrically connected to the computer,
   wherein the computer is configured to:
     calculate a navigation signal from electrical signals obtained from the control electrode and the tip of the catheter; and
     output to the monitor a plurality of positions of the tip of the catheter with respect to the control electrode, wherein the output includes an amplitude of the navigation signal aligned with an R-wave of an electrocardiogram (ECG) signal obtained from the control electrode, and wherein the plurality of positions enables a user to navigate the tip of the catheter to an internal target location.

2. The intravascular catheter navigation device according to claim 1, further comprising a reference electrode electrically connected to the computer, the reference electrode designed for placement on a lower abdomen of the patient.

3. The intravascular catheter navigation device according to claim 1, wherein the navigation signal is calculated as a weighted average of the electrical signals obtained from the control electrode and the tip of the catheter.

4. The intravascular catheter navigation device according to claim 1, wherein the navigation signal is calculated as a weighted difference of the electrical signals obtained from the control electrode and the tip of the catheter.

5. The intravascular catheter navigation device according to claim 1, wherein an enhanced navigation signal is calculated using cross-correlation over several successive periods of the navigation signal.

6. The intravascular catheter navigation device according to claim 1, wherein the output of the plurality of positions of the tip of the catheter with respect to the control electrode includes the amplitude of the navigation signal aligned with a P-wave of the ECG signal obtained from the control electrode.

7. The intravascular catheter navigation device according to claim 6, wherein the output of the plurality of positions of the tip of the catheter with respect to the control electrode includes a weighted average of the amplitudes of the navigation signal aligned with the P-wave, the R-wave, and a T-wave of the ECG signal obtained from the control electrode.

8. The intravascular catheter navigation device according to claim 6, wherein the output of the plurality of positions of the tip of the catheter with respect to the control electrode includes a weighted difference of the amplitudes of the navigation signal aligned with the P-wave, the R-wave, and a T-wave of the ECG signal obtained from the control electrode.

9. The intravascular catheter navigation device according to claim 1, wherein the tip of the catheter is electrically connected to the computer via a conductive solution positioned in a lumen of the catheter.

10. The intravascular catheter navigation device according to claim 1, wherein the tip of the catheter is electrically connected to the computer via a conductive wire.

\* \* \* \* \*